United States Patent [19]
Tachibana et al.

[11] Patent Number: 5,628,728
[45] Date of Patent: May 13, 1997

[54] MEDICINE APPLYING TOOL

[75] Inventors: Katsuro Tachibana; Shunro Tachibana, both of Fukuoka, Japan

[73] Assignee: Ekos Corporation, Everett, Wash.

[21] Appl. No.: 455,444

[22] Filed: May 31, 1995

[51] Int. Cl.⁶ .................................................. A61M 25/00
[52] U.S. Cl. ................................................................ 604/19
[58] Field of Search ............................ 604/21, 19; 601/1; 607/96, 97, 98, 99, 115, 116, 120; 606/32

*Primary Examiner*—Robert A. Hafer
*Assistant Examiner*—Manuel Mendez
*Attorney, Agent, or Firm*—Wilson Sonsini Goodrich & Rosati

[57] ABSTRACT

A medicine applying tool is provided at the tip of a catheter that is used to inject the medicine. An electrode portion has first and second electrodes that are provided so that they interpose a piezoelectric element therebetween. An opening is provided in the vicinity of the electrode portion, and serves to inject a medicine supplied through the catheter into a patient. A third electrode is electrically connected to the patient. An electric signal of an ultrasonic frequency is applied to the first and second electrodes therebetween. A DC voltage is applied to the third electrode and the outside one of the first and second electrodes therebetween.

1 Claim, 5 Drawing Sheets

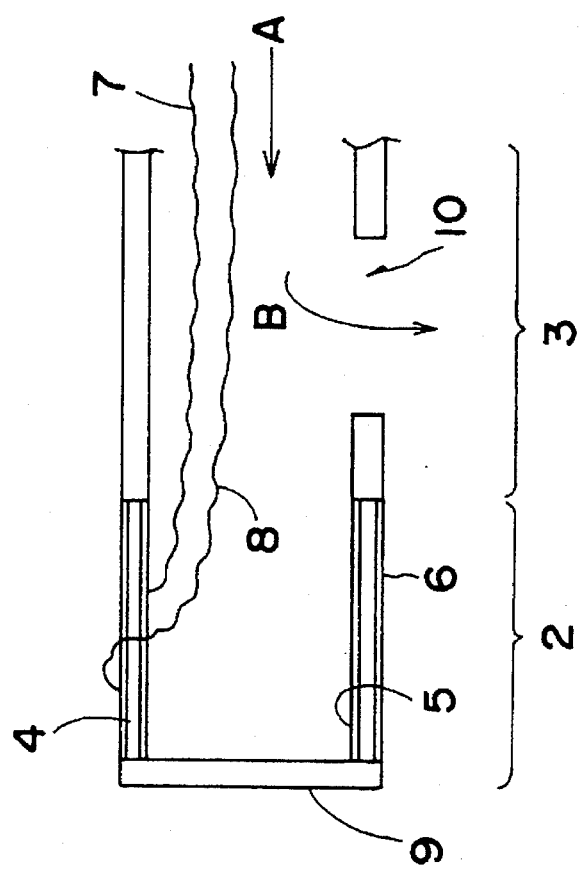
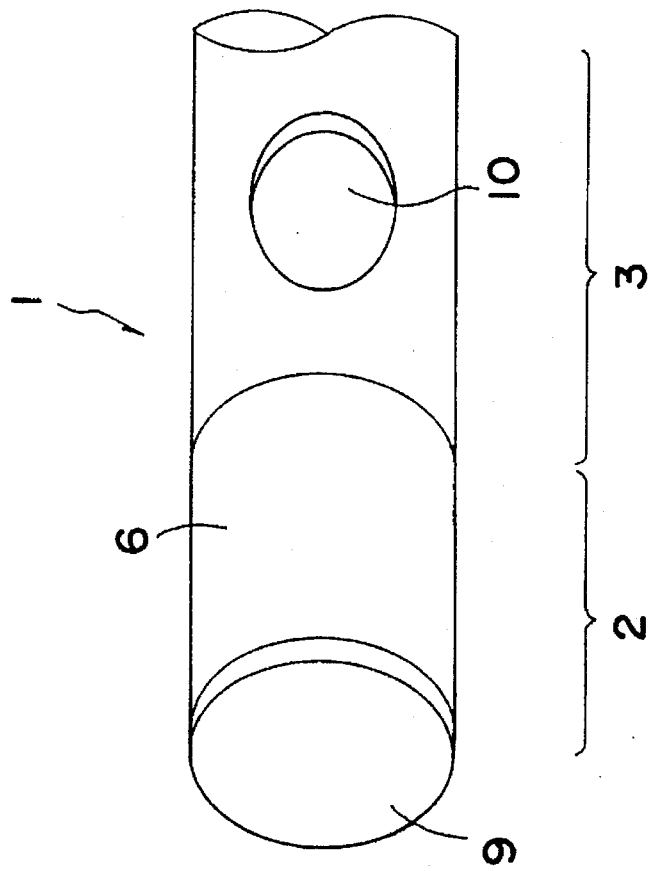

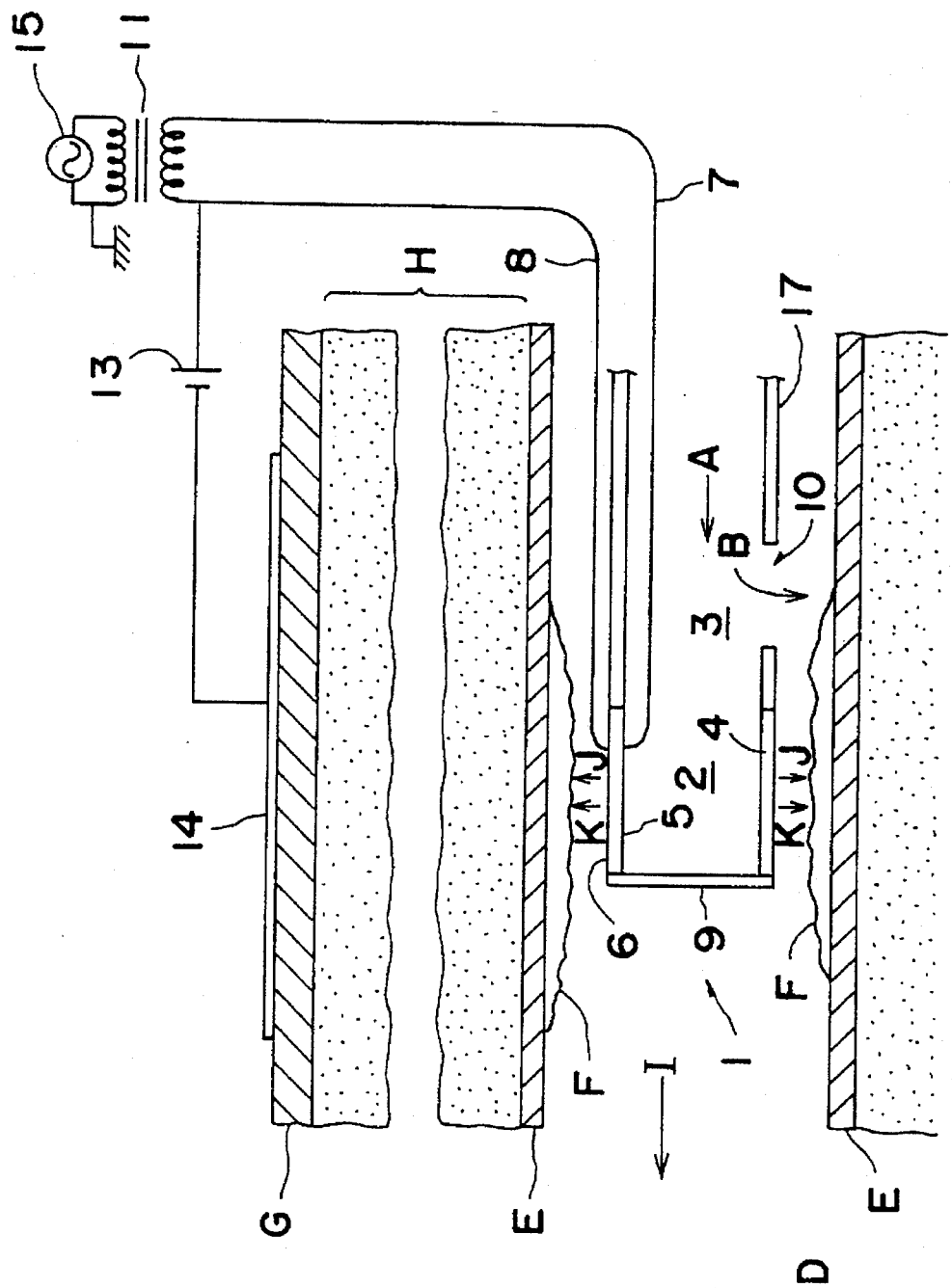

5,628,728

MEDICINE APPLYING TOOL

BACKGROUND OF THE INVENTION

1. Field of the Invention

The present invention relates to a medicine applying tool that is used while mounted on the tip of a catheter, for the purpose of treating various diseases such as thrombosis and arteriosclerosis, and for the treatment of re-occlusion after, for instance, PTCA. In particular, the invention relates to a medicine applying tool that utilizes a combination of ultrasonic waves and electrophoresis.

2. Description of the Prior Art

For example, myocardinal infarct is a disease in which blood flow is restricted by a thrombus or due to arteriosclerosis, so that heart muscles are not supplied with sufficient oxygen and may become necrotic.

Among the treatments for myocardinal infarct is the drug thrombolytic therapy, which is intended to dissolve a thrombus by means of oral application or intravascular injection of a medicine. However, in drug thrombolytic therapy, the medicine is supplied to the affected part by first having the medicine absorbed into the blood and then having the blood circulate through the body. Only a very small amount of the medicine used is absorbed by the affected part. Thus, drug thrombolytic therapy has a problem in that the efficiency in applying a medicine to an affected part is very low. It has a further problem in that the increasing of the density of the medicine to obtain its effective concentration in the blood may cause side effects in other organs.

On the other hand, among the treatments in which a part including a thrombus is treated in a concentrated manner is artery expanding therapy, which is also called PTCA (percutaneous transluminal coronary angioplasty). In the PTCA, a guide catheter is percutaneously introduced to the inlet of the coronary arteries of a patient through a portion of his thigh under X-rays, and then a catheter with a balloon at its tip is introduced, guided by the guide wire, to the part including a pathological change. In this state, the stricture of the coronary artery is relieved by expanding the balloon, to thereby increase the blood flow there.

However, artery expanding therapy has a problem that the probability of restenosis occurring several months after the operation is as high as 30% to 50%. Therefore, reexamination is performed by coronary angiography a predetermined period after the operation. If restenosis is found in the reexamination, the artery expanding therapy is performed again. If the restenosis is not cured, a coronary artery bypass operation is needed, which is much larger in scale.

Further, to prevent restenosis, during artery expanding therapy, a mesh-like cylindrical body called a stent is inserted into the stricture portion of the artery to reinforce the artery wall and the diameter of the cylindrical body is increased by expanding the balloon. However, even in this case, restenosis occurs at a very high frequency.

SUMMARY OF THE INVENTION

An object of the present invention is to provide a medicine applying tool which can efficiently apply a medicine to an affected part, to thereby enhance the effect of treatment.

According to the invention, a medicine applying tool that is provided at the tip of a catheter that is used to inject a medicine, comprises:

a piezoelectric element;

an electrode portion having first and second electrodes that are provided so that they interpose the piezoelectric element therebetween, an electric signal of an ultrasonic frequency being applied to the first and second electrodes therebetween;

an opening provided in the vicinity of the electrode portion, for injecting the medicine supplied through the catheter into a patient; and a third electrode electrically connected to the patient, a DC voltage being applied to the third electrode and the outside one of the first or second electrodes in between.

The medicine is absorbed by the living tissue through an electrophoresis that depends on the density gradient and the voltage difference between the electrodes. In this operation, ultrasonic waves are applied to the part of the body to which the medicine is to be applied. This vibrates the living tissue of that part, and allows the medicine to enter the body tissue more easily. Further, since ultrasonic waves also affect the medicine, the efficiency of diffusion and penetration for the medicine is improved. Further, since ultrasonic waves also affect the electrode, polarization is prevented from occurring in the vicinity of the electrode, and the electrode function can be properly maintained.

BRIEF DESCRIPTION OF THE DRAWINGS

FIGS. 1(a) and 1(b) are a perspective view and a sectional view of a medicine applying tool utilizing ultrasonic waves according to a first embodiment of the present invention;

FIG. 4 schematically shows how thrombosis is treated by using the medicine applying tool of FIGS. 1(a) and 1(b);

DESCRIPTION OF THE PREFERRED EMBODIMENTS

Figure 2:
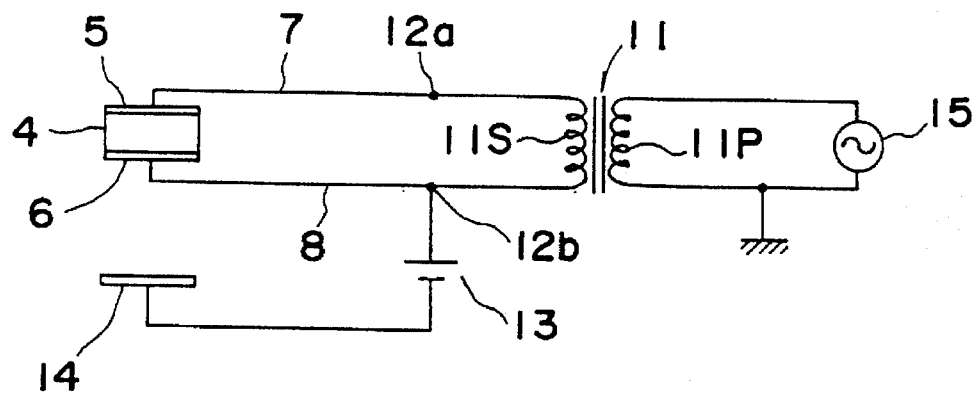
FIG. 2 shows a circuit for generating signals or voltages to be applied to respective electrodes of the medicine applying tool of FIGS. 1(a) and 1(b)

The present invention will be hereinafter described in detail by way of illustrated embodiments.

FIGS. 1(a) and 1(b) are a perspective view and a sectional view of a medicine applying tool utilizing ultrasonic waves according to a first embodiment of the invention. In these figures, a cylindrical medicine applying tool 1 is to be attached to the tip of a catheter that is made of silicone or Teflon and to be inserted into an organ of a human body, or is integral with the tip of the catheter. The medicine applying tool 1 has an electrode portion 2 and a medicine injecting portion 3.

The electrode portion 2 is composed of a cylindrical piezoelectric element 4, a cylindrical inner electrode 5 formed on the inner circumferential surface of the piezoelectric element 4, for instance, by silver evaporation, and a cylindrical outer electrode 6 formed on the outer circumferential surface of the piezoelectric element 4 in the similar manner. The inner electrode 5 is coated with an insulative material and is therefore electrically insulated from the exterior. On the other hand, the outer electrode 6 is electrically exposed to the exterior. Leads 7 and 8, which are connected to the inner electrode 5 and the outer electrode 6, respectively, are led to the proximal end of a catheter through its inside and thereby led out from a human body. The tip portion of the medicine applying tool 1 is covered by a lid 9 that is shaped like a circular plate. For example, the electrode portion 2 has a diameter of about 1 mm and an axial length of about 1 mm. The diameter and the axial length of the electrode portion 1 is in no way limited to such specific dimensions, but can be modified in accordance with the kind and state of an affected part to be treated.

The medicine injecting portion 3 is provided upstream of the electrode portion 2 in a medicine transporting direction (indicated by arrow A). A medicine is jetted from a circular opening 10 of the medicine applying portion 3 in a direction indicated by arrow B.

FIG. 2 shows a circuit for generating signals or voltages to be applied to the respective electrodes. The leads 7 and 8, which are connected at one end to the inner electrode 5 and the outer electrode 6 of the electrode portion 2, are connected at the other end to one terminal 12a of the secondary winding 11S of an insulation transformer 11 and the other terminal 12b, respectively. The terminal 12b is connected, via a DC power supply 13, to a body contact electrode 14 serving as an indifferent electrode. The body contact electrode 14 is brought into close contact with the skin of a patient to be treated to electrically connect one electrode of the DC power supply 13 to the patient's body.

An ultrasonic wave signal source 15 is connected to a primary winding 11P of the insulation transformer 11, and one terminal of the primary winding 11P is grounded.

The DC power supply 13 and the ultrasonic wave signal source 15 are schematically shown in FIG. 2. Actually, the DC power supply 13 may be a variable DC voltage supply device in which the polarity, magnitude and application time of the voltage can be set arbitrarily. The ultrasonic wave signal source 15 may be a programmable ultrasonic wave output device that is composed of a variable frequency oscillator, a variable output amplifying circuit, and other circuits.

Figure 3A:
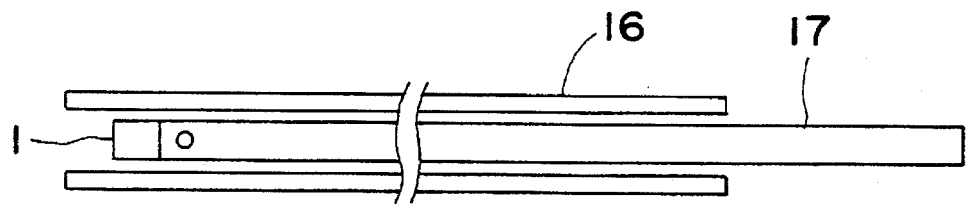
FIGS. 3(a) and 3(b) show how a guide member for introducing the medicine applying tool of FIGS. 1(a) and 1(b) to an affected part is used.
Figure 3B:
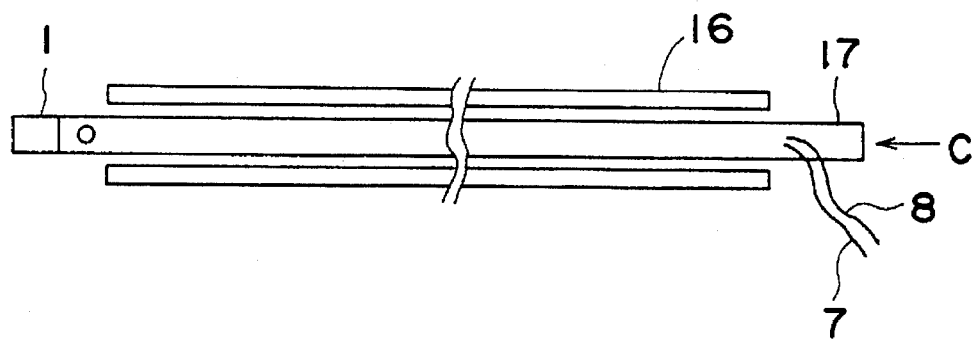

FIGS. 3(a) and 3(b) show how a guide member 16 for introducing the medicine applying tool 1 of FIGS. 1(a) and 1(b) to an affected part is used. The guide member 16 is a flexible pipe whose inside diameter is somewhat larger than the outside diameter of a catheter 17 that has the medicine applying tool 1 at its tip. First, as shown in FIG. 3(a), while the medicine applying tool 1 is incorporated in the guide member 16, force is applied to the guide member 16 to move it through the blood vessels until its tip reaches the vicinity of the affected part. In this operation, the catheter 17 moves together with the guide member 16. The guide member 16 is moved in the direction of the blood flow to facilitate insertion. When the tip of the guide member 16 has reached the vicinity of the affected part, force is applied only to the catheter 17, to thereby project the medicine applying tool 1 from the tip of the guide member 16 (see FIG. 3(b)). Then, a prescribed signal is applied to the leads 7 and 8 that are led out from the proximal end of the catheter 17 in a fluid-tight state, and a medicine is injected from the proximal end of the catheter 17 as indicated by arrow C.

The proximal end of the catheter 17 is connected to a medicine supply tank directly or via a detachable coupler. Alternatively, an open/close-switchable plug may be provided at the proximal end of the catheter 17. The medicine is injected by use of a syringe or the like with the plug opened. During application of the medicine, the plug is closed.

FIG. 4 schematically shows how thrombosis is treated by using the medicine applying tool 1 of FIGS. 1(a) and 1(b). In FIG. 4, reference characters D denotes a blood vessel; E, a wall of the blood vessel D; F, a thrombus formed on the wall E; G, a skin; H, body tissue between the blood vessel D and the skin G; and I, a direction of the blood flow.

FIG. 4 shows a state where the electrode portion 2 of the medicine applying tool 1 is moved to a position opposed to the affected part, i.e., the thrombus F. As shown in FIG. 3(b), when a medicine in the form of a solution for thrombosis treatment is injected into the inside of the catheter 17 from its proximal end, it moves through the catheter 17 and reaches the medicine applying tool 1 attached to the catheter's tip. Since the tip of the medicine applying tool 1 is covered by the lid 9, and the opening 10 is formed in the medicine injecting portion 3, the medicine that has been transported through the catheter 17 in the direction indicated by arrow A is injected into the blood vessel D as indicated by arrow B. The medicine then flows toward the thrombus F being carried by the blood stream, and components of the medicine are brought into contact with the surface of the thrombus F.

In the electrode portion 2, an electric signal of an ultrasonic frequency is applied to the inner electrode 5 and the outer electrode 6 in between, so that the piezoelectric element 4 vibrates mechanically at the ultrasonic frequency. The ultrasonic vibration is applied to the thrombus F and the medicine in the vicinity thereof. Since the ultrasonic vibration is emitted from the piezoelectric element 4 perpendicularly to its surface, i.e., to the axis of the electrode portion 2 as indicated by arrow J, it acts on the thrombus F efficiently.

Under application of the ultrasonic vibration, tissue of the thrombus F is loosened to absorb the medicine more easily.

Further, since DC voltage is applied to the outer electrode of the electrode portion 2 and the body contact electrode 14 in between, a current flows in the direction of the positive electrode of the DC power supply 13→lead 8→outer electrode 6→blood→thrombus F→blood vessel wall E→body tissue H→body contact electrode (indifferent electrode) 14→negative electrode of the DC power supply 13 as indicated by arrow K. Assisted by the flow of this current, the components of the medicine penetrate the thrombus F. Thus, it is possible to make the medicine efficiently penetrate the thrombus F by utilizing the ion migration method known as iontophoresis.

Iontophoresis is one of the methods for increasing the absorption rate, and is described in, for instance, Morimoto: "Development of TTS derivatives in the U.S.," Therapeutic Research, Vol. 10, No. 3, pp. 169 (889)–180 (900), 1989. Iontophoresis, which is also called the ion introduction method or ion penetration method, is a kind of electrical therapy in which a certain amount of medicine is introduced into a living body without causing pain, through a skin or a mucous membrane, being aided by a DC current ("Medical Dictionary," Nanzando Company, Ltd., published Apr. 10, 1974). Iontophoresis provides an advantage of facilitating absorption of medicine, because the absorption is effected by electrophoresis in addition to the density gradient.

The application of ultrasonic waves has the effect of reducing the voltage that is necessary for the iontophoresis, eliminating the possibility of inducing irregular pulses even where the treatment is performed near the heart.

Further, since the invention can provide more effective treatment with a lower dosage of medicine, side effects are reduced accordingly.

Since a DC voltage is applied to outer electrode 6, polarization occurring in the vicinity of the surface of the outer electrode might lower the efficiency of an injected medicine because of a voltage difference. However, in this embodiment, since ultrasonic waves are also applied to the outer electrode 6, minute liquid flows occurring in the vicinity of the surface of the outer electrode 6 cancel the polarization. Thus, there is no possibility that the electrode function of the outer electrode 6 will be lowered.

Figure 5:
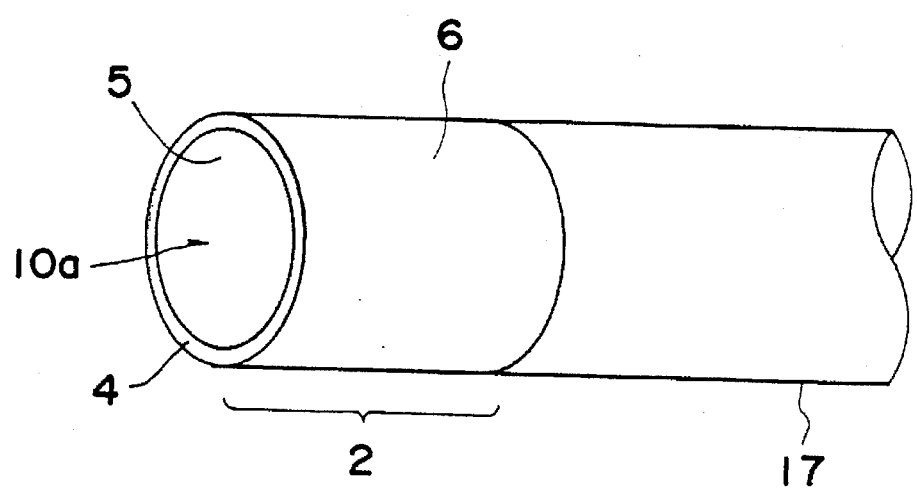
FIG. 5 is a perspective view of a second embodiment of the invention.

FIG. 5 is a perspective view of a second embodiment of the invention. This embodiment is different from the first embodiment in that an opening 10a is formed in the tip portion (rather than in the side wall) of the medicine applying tool 1; that is, the tip portion of the medicine applying tool 1 becomes the medicine injecting portion. The medicine applying tool 1 of the second embodiment operates in approximately the same manner as the first embodiment. In the second embodiment, since the tip of the catheter 17 is opened, the catheter 17 can be guided with a guide wire (not shown) passed through it. In this case, since the guide member 16 of FIGS. 3(a) and 3(b) need not be provided outside the catheter 17, the medicine applying tool 1 can be inserted into thinner blood vessels.

Figure 6:
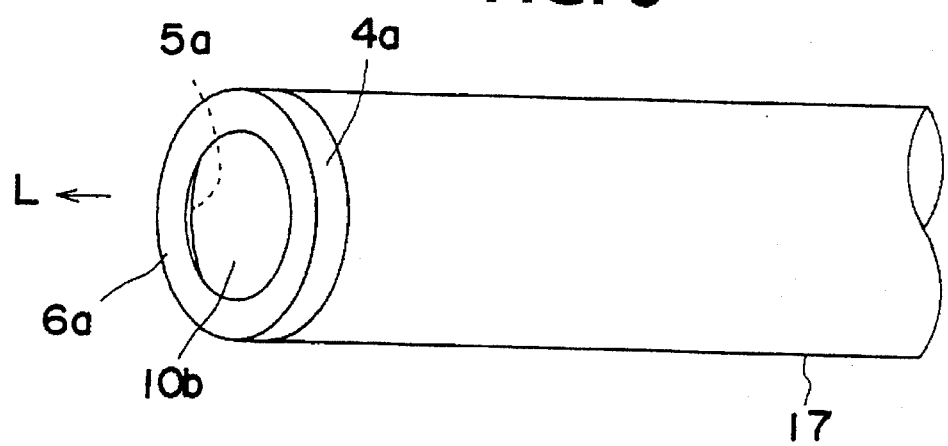
FIG. 6 is a perspective view of a third embodiment of the invention.

FIG. 6 is a perspective view showing a third embodiment of the invention. In this embodiment, the electrode portion is composed of a flat, annular piezoelectric element 4a, an annular inner electrode 5a that is attached to the inner surface of the piezoelectric element 4a, and an annular outer electrode 6a that is formed on the outer surface of the piezoelectric element 4a. The surface of the inner electrode 5a is covered with an insulating material so that the inner electrode 5a is electrically insulated from the exterior. On the other hand, the outer electrode 6a is electrically exposed to the exterior.

In the third embodiment, an opening 10b is provided inside the piezoelectric element 4a and the electrodes 5a and 5a. A medicine is jetted forward (indicated by arrow L) from the opening 10b. Since the piezoelectric element 4a vibrates in the axial direction of the catheter 17, ultrasonic energy is also emitted in a forward direction (indicated by arrow L). In this embodiment, as in the case of the second embodiment, the catheter 17 can be guided by a wire, because the opening 10b is formed inside the piezoelectric element 4a and the electrodes 5a and 6a.

Figure 7:
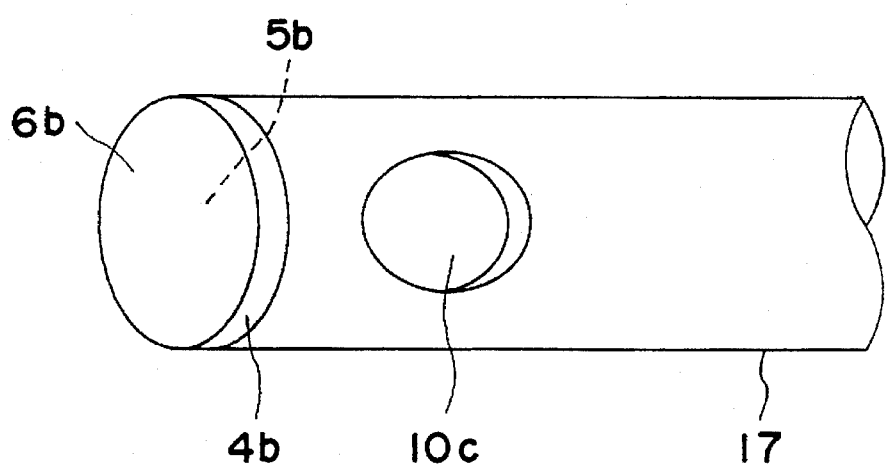
FIG. 7 is a perspective view of a fourth embodiment of the invention.

FIG. 7 is a perspective view showing a fourth embodiment of the invention. In this embodiment, the electrode portion is composed of a disc-shaped piezoelectric element 4a, a disc-shaped inner electrode 5a that is attached to the inner surface of the piezoelectric element 4a, and a disc-shaped outer electrode 5a that is formed on the outer surface of the piezoelectric element 4a. The tip portion of the catheter 17 is covered by the electrode portion. In the fourth embodiment, an opening 10c for jetting a medicine is formed in the side wall of the catheter 17. A medicine is jetted sideways while ultrasonic waves are emitted in a forward direction.

Figure 8:
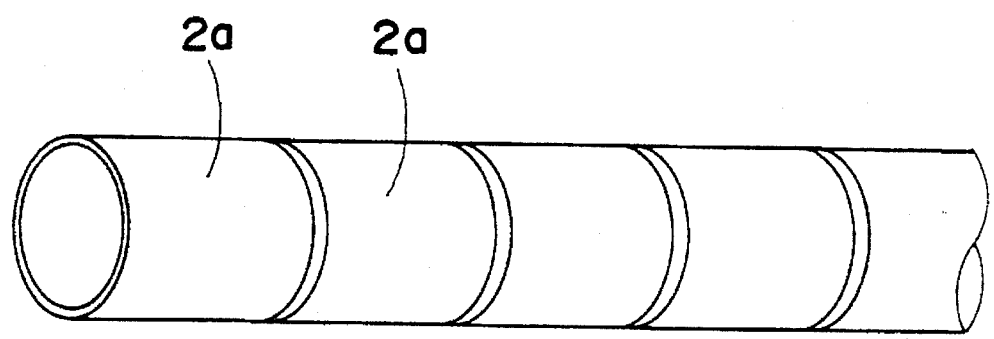
FIG. 8 is a perspective view of an embodiment in which a plurality of divisional electrode portions are provided along the axis of a catheter.
Figure 9:
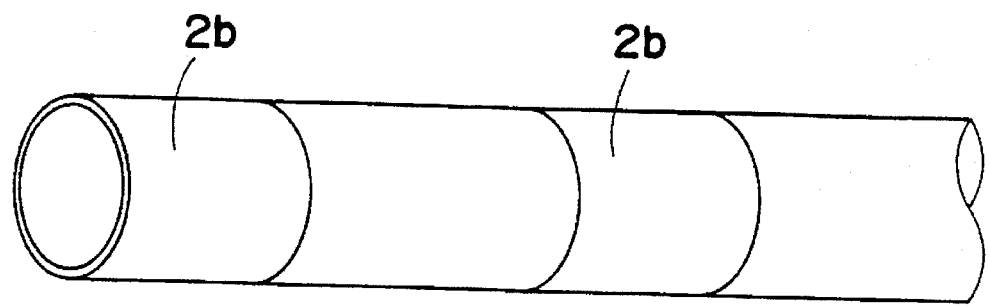
FIG. 9 is a perspective view of an embodiment in which a plurality of electrode portions are provided along the axis of a catheter at predetermined intervals.
Figure 10:
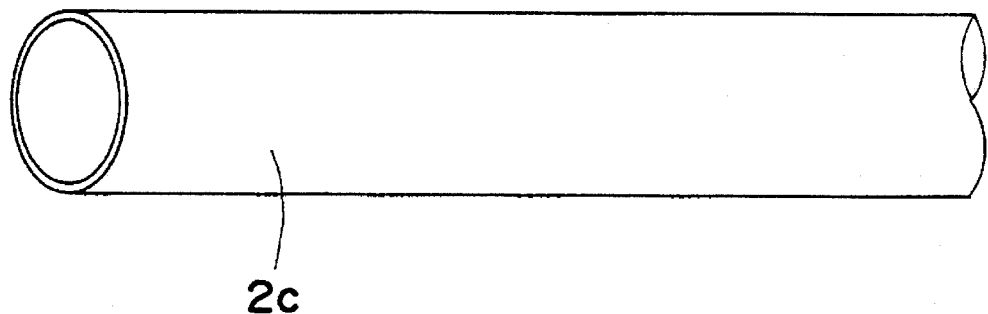
FIG. 10 a perspective view of an embodiment in which a piezoelectric element of an electrode portion is a flexible film.

Although, in the above embodiments, only one electrode is provided at the tip of the catheter, a plurality of divisional electrode portions 2a may be provided along the axis of the catheters as shown in FIG. 8, or a plurality of electrode portions 2b may be provided along the axis of the catheter at predetermined intervals as shown in FIG. 9. The reason why the divisional electrode portions are provided along the axis of the catheter in the above manner is that, if a long electrode portion having a piezoelectric element that is usually not flexible is provided along the axis of the catheter, the flexibility of the catheter is lost. However, by employing as the piezoelectric element a flexible film made of a piezoelectric material such as a fluorine compound, a long electrode portion can be provided along the axis of the catheter as shown in FIG. 10.

Although the above embodiments are directed to those cases where the medicine applying tool is inserted into a blood vessel, the invention is not limited to this manner. It is applicable to other cases where it may be inserted into a digestive tract or a tumor.

Examples of medicines that can be injected by use of the medicine applying tool of the invention are heparin, hirudin, urokinase, and photofrin (ultrasonic-wave-sensitive medicine).

As described above, according to the invention, a medicine is applied to an affected part being assisted by iontophoresis and application of ultrasonic waves. In this way, the efficiency of a medicines application can be greatly improved over the cases where components of a medicine are penetrated only by its osmotic pressure. Further, since one of the electrodes for emission of ultrasonic waves is also used as the electrode for iontophoresis, the tool has a simple configuration.

What is claimed is:

1. A medicine applying tool, comprising:

a catheter including a distal portion and an injection port configured to deliver a medicine introduced through the catheter to the injection port;

a piezoelectric element that includes an exterior surface and an interior surface formed in an interior of the piezoelectric element;

an electrode portion coupled to the distal portion of the catheter, the electrode portion having a first electrode positioned at the exterior surface of the piezoelectric element and a second electrode positioned at the interior surface of the piezoelectric element, wherein the first and second electrodes are configured to receive an electric signal of an ultrasonic frequency applied to the first and second electrodes; and a third electrode, electrically connected to the patient, wherein a DC voltage is applied to the third electrode and not to the first and second electrodes.

* * * * *

UNITED STATES PATENT AND TRADEMARK OFFICE
CERTIFICATE OF CORRECTION

PATENT NO. : 5,628,728
DATED : May 13, 1997
INVENTOR(S) : Katsuro Tachibana and Shunro Tachibana It is certified that error appears in the above-identified patent and that said Letters Patent is hereby corrected as shown below:

<u>Title page</u>
Item [73], Assignee, delete "Ekos Corporation, Bothell, WA (US)"

Signed and Sealed this

First Day of June, 2004

JON W. DUDAS
*Acting Director of the United States Patent and Trademark Office*